United States Patent
Bansleben et al.

(10) Patent No.: US 6,573,345 B1
(45) Date of Patent: Jun. 3, 2003

(54) CATALYST COMPOSITIONS AND PROCESSES FOR OLEFIN OLIGOMERIZATION AND POLYMERIZATION

(75) Inventors: Donald Albert Bansleben, Columbia, MD (US); Stefan K. Friedrich, San Gabriel, CA (US); Todd Ross Younkin, Pasadena, CA (US); Robert Howard Grubbs, South Pasadena, CA (US); Chunming Wang, Highland Park, NJ (US); Robert Tan Li, Longview, TX (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 09/007,442

(22) Filed: Jan. 15, 1998

Related U.S. Application Data

(63) Continuation-in-part of application No. 08/822,536, filed on Mar. 24, 1997, now abandoned.

(51) Int. Cl.[7] .............................. C08F 4/64; C08F 4/642; C08F 4/70
(52) U.S. Cl. ........................... 526/161; 526/91; 526/93; 526/123.1; 526/124.1; 526/141; 526/147; 526/169.1; 526/171; 526/172; 502/117; 502/155
(58) Field of Search .............................. 526/161, 169.1, 526/172, 91, 93, 123.1, 124.1, 141, 147, 171

(56) References Cited

U.S. PATENT DOCUMENTS

| | | | |
|---|---|---|---|
| 3,635,937 A | | 1/1972 | Bauer et al. |
| 3,644,563 A | * | 2/1972 | Bauer et al. |
| 3,647,915 A | | 3/1972 | Bauer et al. |
| 3,678,022 A | * | 7/1972 | Bozik et al. ............... 260/88.7 |
| 3,686,159 A | | 8/1972 | Bauer et al. |
| 4,293,502 A | * | 10/1981 | Beach et al. |
| 4,293,727 A | * | 10/1981 | Beach et al. |
| 4,301,318 A | * | 11/1981 | Beach et al. |
| 4,310,716 A | * | 1/1982 | Beach et al. |
| 4,382,153 A | * | 5/1983 | Beach et al. |
| 4,533,651 A | | 8/1985 | Masters et al. |
| 4,537,982 A | | 8/1985 | Starzewski et al. |
| 4,680,354 A | * | 7/1987 | Lin et al. .................... 526/172 |
| 5,210,360 A | | 5/1993 | Wu |
| 5,282,696 A | | 2/1994 | Solomon et al. |
| 5,539,124 A | | 7/1996 | Etherton et al. |
| 5,557,023 A | | 9/1996 | Somogyvari et al. |
| 6,174,975 B1 | * | 1/2001 | Johnson et al. ............. 526/172 |

FOREIGN PATENT DOCUMENTS

| | | |
|---|---|---|
| WO | WO 96/23010 | 8/1996 |
| WO | 98/30609 | * 7/1998 |

OTHER PUBLICATIONS

Bolm, C.; Weickhardt, K.; Zehnder, M.; Clasmacher, D.; Helv. Chim. Acta 1991, 74, 717–726.*
Freitas, E.R., Gum, C.R., Chem. Eng. Prog. Jan. 1979. pp 73–76.*
Keim, W.; Kowaldt, R.; Goddard, R.; Kruger, C. Angew. Chem., Int. Ed. Engl. 1978, 17, 466–467.*
Van Hecke, G.R.; Horrocks, W.D.; Inorganic Chem. 1966, 5, 1968–1974.*
Miyashita, N.; Yoshikoshi, A.; Grieco, P.A.; J. Org. Chem. 1977, 42, 3772–4.*
Klabunde, U.; Mulhaupt, R.; Herskovitz, T.; Janowicz, A. H.,; Calabrese, J.; Ittel, S.D.; J. Polymer Sci. Part A; Polymer Chemistry 1987, 25, 1989–2003.*
Johnson, L.K.,; Killian, C.M.; Brookhard, M.J.; Am. Chem. Soc. 1995, 117, 6414–6415.
Klabunde, U.; Ittel, S.D. J. Molecular Catal. 1987, 41, 123–134.
Booth, G.; Chatt, J. J. Chem. Soc. 1965, 3238–3241.
Hidai, M.; Kashiwagi, T.; Ikeuchi, T.; Uchida, Y.; J. Organomet. Chem. 1971, 30, 279–282.
Heck, R.F.; J. Am. Chem. Soc. 1963, 85, 2013–2014.
Casirighi, G.; Casnati, G.; Puglia, G.; Sartori, G.; Terenghi, G.; J. Chem. Soc., Perkin Trans. I 1980, 1862–5.
Hoyer, S.; Laszlo, P. Synthesis 1986, 655–7.
Rice, J.E.; Cai, Z.W.; J. Org. Chem 1993, 58, 1415–1426.
Narasimhan, N.S.; Mali, R.S.; Barve, M.V.; Synthesis Nov. 1979, 906–9.

* cited by examiner

Primary Examiner—David W. Wu
Assistant Examiner—R. Rabago

(57) ABSTRACT

The present invention is directed to processes of polymerizing olefin monomers and copolymerizing olefin monomer (s) with functionalized alpha-olefin monomers in the presence of certain late transition metal pyrrolaldimine chelates, especially bidenate

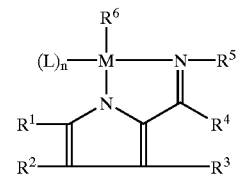

or in the presence of a combination of a transition metal in its zero valence and a pyrrolaldimine represented by the formula:

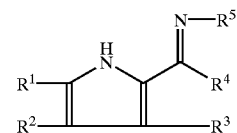

wherein each $R^1$, $R^2$, $R^3$, $R^4$, $R^5$, $R^6$, M and L are defined in the specification herein below.

125 Claims, No Drawings

CATALYST COMPOSITIONS AND PROCESSES FOR OLEFIN OLIGOMERIZATION AND POLYMERIZATION

This application is a continuation-in-part application of U.S. application Ser. No. 08/822,536, filed Mar. 24, 1997 now abandoned.

This invention was made with United States Government support under Contract No. 70NANB5H1136 awarded by the Department of Commerce's National Institute of Standards and Technology. The United States has certain rights in the invention.

The present invention is directed to organometallic catalysts and catalyst compositions useful in the oligomerization or polymerization of alpha-olefins alone or in combination with functionalized olefins, certain bidentate ligand compounds useful in providing the subject catalysts, processes of forming the bidentate ligand compounds and catalysts therefrom, processes of forming olefin oligomers and polymers utilizing the subject catalysts, and catalyst compositions and the oligomers and polymers formed therefrom.

The polyolefin industry has relied on various catalyst and initiator systems. The polymerization of ethylene and other non-polar 1-olefins has been commonly accomplished using organometallic Ziegler-Natta coordination-type catalysts, chromium catalysts, other early transition metal catalysts as well as free-radical type initiators. Although the array of catalysts available provides different approaches to the manufacture of polyolefins with differing physical and mechanical properties, these catalysts are highly susceptible to a range of substances which poison or deactivate the catalyst's activity. It is well known that even trace amounts of oxygen, carbon monoxide, acetylene or water causes deactivation. Further, catalyst deactivation is caused by organic compounds having oxygen donor groups such as ethers, esters, alcohols, or ketones. Industrial application of these organometallic catalysts requires careful and elaborate measures to assure the absence of such poisons. Because these catalysts are easily poisoned, they tend to form low molecular weight materials, can not be used to provide copolymerization of ethylene with an oxygenated functional monomer, such as an ester, acid or ether functionalized olefin, and generally may produce highly branched polymer products.

More recently, olefin polymerizaton catalysts have been developed which are less oxophilic than the early transition metal counterparts. For example, U.S. Pat. Nos. 4,310,716; 4,382,153; 4,293,727; 4,301,318; and 4,293,502 each disclose late transition metal (e.g. Ni) complexes which provide low molecular weight oligomers of ethylene. Further, polymerization of ethylene has been successfully shown using complexes based on phosphorus ylide ligands in U.S. Pat. No. 4,537,982 as well as in U.S. Pat. Nos. 4,698,403; 4,716,205; and 4,906,754. These nickel based catalysts formed from P-O bidentate ligands have been shown to provide high activity in the oligomerization and polymerization of ethylene. Still more recently, L. K. Johnson et al in J. Am. Chem. Soc. 1995 117, 6414, reported the formation and use of Pd(II) and Ni(II) based cationic complexes formed from diimine ligands to provide high molecular weight polyolefins. Finally, WO 96/23010 describes a process for the polymerization of olefins using a variety of transition metal complexes of certain diimine bidentate ligands. In many cases the polymerization provided highly branched polyolefins and were not shown to be useful in providing functionalized copolymer products. Further, in those instances where functionalized copolymers were formed, it was shown that the functional groups reside exclusively at the end of chain branches.

Certain processes and cationic nickel (II) catalyst compositions have been described also by L. K. Johnson et al in WO 97/02298. These cationic complexes are described as active for the polymerization of ethylene and other olefins. They require use of an acid of a non-coordinating monoanion, or some combination of compounds that will generate such acid, in order for the catalyst composition to be rendered active towards olefin polymerization. The present neutral complexes, as well as the use of a Lewis base is not suggested by Johnson et al.

Löfgren et al, in Macromolecules 1997, 30, 171-175 describe polymerization of ethylene by cationic zirconium salen bis-chloride complexes with or without a Lewis base (tetrahydrofuran). They show that the catalyst composition exhibits only low levels of activity. There are many references to the deleterious effect of Lewis base toward late transition metal catalyst compositions as well as single-site catalyst compositions of the metallocene type. For example, EP 94/304642 and EP 94/630910 disclose that Lewis base, such as dialkyl ether, substantially terminates olefin polymerization by a single-site catalyst composition composed of a metallocene compound and partially hydrolyzed aluminum alkyl compound (aluminoxane). Additionally, U.S. Pat. No. 5,571,881 and WO 95/14048 indicate that an unsaturated Lewis base, e.g., vinyl ether, either reacts with the cationic late transition metal catalysts to destroy their activity or causes reduction of the resultant polymer molecular weight. It is highly desired to provide a catalyst for the oligomerization and polymerization of olefins, in particular ethylene, which provides a substantially linear (low degree of branching) product. It is also highly desired to provide a nonionic catalyst which can provide the linear polymer product. It is still further desired to provide a nonionic catalyst which is capable of providing a product of high molecular weight which is substantially linear and, optionally, which is capable of promoting copolymerization of olefin and functionalized olefin monomer units.

Finally, it is desired to provide a catalyst composition composed of a non-ionic catalyst in combination with an adjunct agent and/or a Lewis base which is capable of providing a product of high molecular weight which is substantially linear and, optionally, which is capable of promoting copolymerization of olefin and functionalized olefin monomer units.

SUMMARY OF THE INVENTION

The present invention is directed to certain late transition metal pyrrolaldimine chelates as olefin oligomerization or polymerization catalysts, to the bidentate ligand compounds of substituted pyrrolaldimine which are precursors for said catalysts, to catalyst compositions composed of said pyrrolaldimine chelates in combination with an adjunct agent and/or a Lewis base, the methods of forming said precursor compounds and said catalysts, and the method of polymerizing olefin monomers, especially ethylene, as well as copolymerization of olefin and functionalized olefin monomers. Each of the above elements of the present invention is fully described herein below.

DETAILED DESCRIPTION

The present invention provides a process for polymerizing olefin monomers, in particular ethylene, in the presence of catalysts taken from the selected family of pyrrolaldimine late transition metal chelates and to catalyst compositions composed of said pyrrolaldimine chelates in combination with an adjunct agent and/or a Lewis base, to produce olefin oligomers or polyolefins which can be either substantially linear and have a weight average molecular weight of at least 150.

It has been presently found that certain pyrrolaldimine late transition metal chelates can provide catalyst systems for the oligomerization or homopolymerization of ethylene and copolymerization of ethylene and functionalized olefins to provide substantially linear polymer products. The catalyst of the present invention can be represented by the following

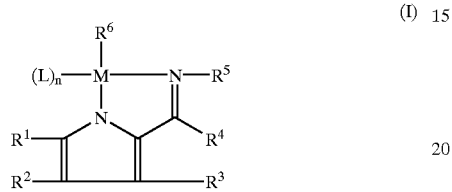

(I)

wherein $R^1$ represents a hydrogen atom, $C_1$–$C_{11}$ alkyl (preferably $C_1$–$C_5$ and most preferably tert-butyl); aryl, such as phenyl, biphenyl, terphenyl, naphthyl, anthracyl, phenanthracyl and the like; substituted aryl wherein the substitution group is selected from $C_1$–$C_6$ alkyl, perfluoroalkyl, nitro, sulfonate, or halo group; arylalkyl, such as toluyl and the like; halo, such as chloro, bromo, and the like; nitro group; sulfonate group or siloxyl (—$OSiA_3$ where A is selected from phenyl or $C_1$–$C_4$ alkyl such as isopropyl or butyl and the like); or a hydrocarbyl terminated oxyhydrocarbylene group, —$(BO)_zR^7$, wherein each B independently represents a $C_1$–$C_4$ (preferably $C_2$–$C_3$) alkylene group or an arylene group (preferably phenyl, especially the B group adjacent to the base structure to which $R^1$ is bonded); $R^7$ represents a $C_1$–$C_{11}$ (preferably a $C_1$–$C_3$) hydrocarbyl group such as an alkyl or an unsubstituted or substituted aryl group, such as phenyl, biphenyl, naphthyl and the like, alone or substituted with one or more $C_1$–$C_6$ alkyl; and z is 1 to 4, $R^1$ is preferably a steric bulky group selected from aryl, substituted aryl or a branched $C_3$–$C_6$ alkyl group and most preferably, phenyl, anthracyl, phenanthracyl, terphenyl or t-butyl:

$R^2$ represents hydrogen atom, aryl, substituted aryl, $C_{1-C11}$ alkyl, halogen atom or $R^1$ and $R^2$ can, together provide a hydrocarbylene or substituted hydrocarbylene which forms a carbocyclic ring which may be non-aromatic or aromatic; $R^2$ is preferably hydrogen or, taken with $R^1$ as a carbocyclic ring group:

$R^3$ represents hydrogen:

$R^4$ represents hydrogen atom, a $C_1$–$C_{11}$ alkyl, an aryl group such as a phenyl or a substituted aryl group such as 2,6-dimethylphenyl or the like, and is preferably selected from hydrogen, $R^5$ represents a $C_1$–$C_{11}$ alkyl group (preferably a $C_4$–$C_8$ alkyl group) such as methyl, ethyl, propyl, t-butyl, and the like, a cycloalkyl group such as cyclohexyl and the like, an aryl group, such as phenyl, biphenyl, naphthyl or the like or a substituted aryl having one or both ortho positions of the aromatic group (especially the phenyl group) substituted with a $C_1$–$C_4$ alkyl and/or the para position (with respect to the N—$R^5$ bond) substituted with a hydrogen atom, nitro, trifluoromethyl, halogen atom, methoxy, or $C_1$–$C_4$ alkyl or fused or unfused aryl, sulfonate, or a hydrocarbyl terminated oxyhydrocarbylene group, —$(BO)_zR^7$ as defined in $R^1$ above. $R^5$ is preferably a t-butyl or a cycloalkyl such as adamantyl, or a 2,6-di($C_1$–$C_4$ alkyl)phenyl group and most preferably 2,6-diisopropyl phenyl or 2,6-diisopropyl-4-nitrophenyl:

$R^1$ and $R^5$ can, together, form an oxyhydrocarbylene chain, e.g., —$(BO)_mB$— wherein each B independently represents a $C_1$–$C_3$ alkylene group or an arylene group and m is an integer of from 2 to 5 preferably 3–5;

n is an integer of 0 or 1;

$R^6$ represents, when n is 1, an unsubstituted or substituted aromatic group, such as phenyl which is preferably unsubstituted, a $C_1$–$C_{11}$ alkyl (preferably a $C_1$–$C_5$ alkyl and most preferably methyl), a hydrogen atom or halogen atom (preferably chloro or bromo), or when n is 0, $R^6$ repesents an allyl or substituted allyl group wherein the substitution can be selected from a halogen atom, a nitro group or a sulfonate group:

L represents a coordination ligand such as triphenylphosphine, tri($C_1$–$C_6$ alkyl) phosphine, tricycloalkyl phosphine, diphenyl alkyl phosphine, dialkyl phenylphosphine, trialkylamine, arylamine such as pyridine, $C_2$–$C_{20}$ alkene such as octene, decene, dodecene, alkyl and the like, a substituted alkene wherein the substitution group may be selected from a halogen atom (preferably chloro), an ester group, a $C_1$–$C_4$ alkoxy group, an amine group (—$NR_2$ wherein each R is hydrogen, or a $C_1$–$C_3$ alkyl), carboxylic acid or its alkali metal salt, di($C_1$–$C_3$)alkyl ether, tetrahydrofuran, a nitrile such as acetonitrile and the like:

M represents one of the transition metals, that is a Group VIII or Group IV transition metal selected from Fe, Co, Ni, Ru, Rh, Pd, Os, Ir, Pt in the +2 oxidation state or Ti, Zr, Hf in the +4 oxidation state and preferably a late transition metal selected from iron, cobalt, nickel or palladium and most preferably either nickel or palladium.

The present invention provides a catalyst which contains sterically bulky groups both above and below as well as within the plane of orientation with respect to the transition metal of the complex. It is believed, though not meant to be a limitation of the invention, that the steric and electronic configuration of the presently achieved complex provides the following desired characteristics:

(1) it utilizes late transition metals (preferably Ni or Pd) to provide high resistance to deactivation by oxygenated species;

(2) it contains certain bidentate, chelating ligand groups which are believed to enhance the selectivity-controlling effect in the polymerization of ethylene and of α-olefins;

(3) it contains groups of extreme steric bulk which provide shielding or partial shielding of the axial faces of the transition metal (II) square planar complexes and thereby it is believed, retards associative displacement and chain transfer during the polymerization; and (4) the steric bulk which is within the plane of the transition metal (II) square planar complex may inhibit chain migration processes and thereby cause substantially linear polymerization.

(5) the steric bulk which is within the plane of the transition metal (II) square planar complex may promote dissociation of the ancillary ligand, L, and thereby result in an increase in the number of active polymerization sites.

The catalysts (I) are most preferably those having bulky substituents, such as aryl as, for example, anthracenyl, phenanthracenyl, or terphenyl and the like, and substituted aryl groups such as 2,6-diisopropylphenyl and the like, in the $R^1$ and/or $R^5$ positions. The substitution group may be a $C_1$–$C_4$ alkyl and/or an electron withdrawing group such as $NO_2$, halogen, sulfonate ($SO_3^-$), sulfonyl ester ($SO_2R$), carboxyl ($COO^-$), or perfluoroalkyl group.

The catalyst (I) of the present invention may further contain an ether or polyether group as part of structure of the subject pyrrolaldimine. The incorporation of such group(s) can be made at $R^1$ and/or at $R^5$ or as an oxyhydrocarbylene chain between $R^1$ and $R^5$ such that a hydrocarbon moiety of said oxyhydrocarbylene is directly bonded to the nitrogen atom at $R^5$ and to the ring at $R_1$. Such catalysts provide enhanced catalytic activity over catalyst (I) absent said group(s) and do not require the use of adjunct agent or Lewis base additive, as described herein below.

Synthesis of the precursor ligands can be achieved by reacting the appropriate pyrrole-2-carboxaldehyde (having desired substituent groups on the pyrrole ring) with a primary amine ($R^5NH_2$), such as 2,6-diisopropylaniline and the like. The reaction can be carried out in solution with an inert solvent, such as a $C_1$–$C_5$ alcohol (e.g. methanol, ethanol or the like) or aromatic compound (e.g., benzene, toluene or the like). The reaction is preferably carried out at temperatures of from about 15° C. to 80° C. (most preferably at from 15 to 25° C.) for a period of from one to twenty hours (most preferably from 10 to 12 hours). The reaction is carried out at atmospheric pressure and in the presence of a catalytic amount of an organic acid, such as toluenesulfonic acid to provide the pyrrole-2-carboxaldehyde ligand (IV) according to the equation below:

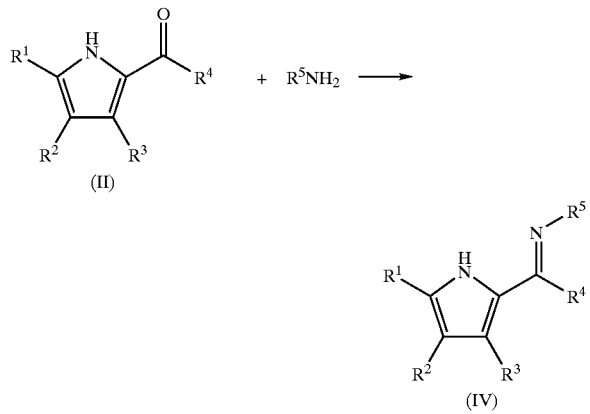

The bidentate ligand (IV) can be deprotonated using a strong alkali metal alkyl, such as a lithium alkyl (e.g., n-butyl Li) to form the alkali metal (e.g., lithium) salt (V). The deprotonation is carried out at low temperatures such as about 0° to 30° C. (preferably 0° to 10° C.) at normal atmospheric pressure and in the presence of an inert solvent, such as tetrahydrofuran, dialkyl ether, $C_5$–$C_{10}$. hydrocarbon, dioxane and the like. The reaction normally is completed in a short period, such as from about 5 to 30 minutes. The lithium salt (V) can then be reacted with a late transition metal coordination compound of the type $R^6(L)_2MY$, wherein each $R^6$ and L are as defined above, and Y represents a halogen atom, as for example bis(triphenylphosphine) phenyl nickel chloride, and the like. This reaction may be conducted in an inert solvent, such as tetrahydrofuran, dialkyl ether, $C_5$–$C_{10}$ hydrocarbon, and the like at temperatures of from about 10 to 90° C. (preferably 10° to 30° C.) for periods of from one to fifteen hours (normally 10–15 hours) to provide catalyst (I) as follows:

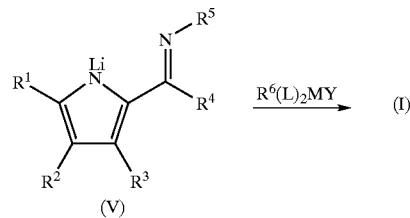

In the above, the $R^1$ may be hydrogen but preferably is a bulky group which provides a steric shield of the transition metal's equatorial face by being well-positioned in the plane of the transition metal complex as well as some bulk in the axial face. For example, $R^1$ is preferably an aryl, such as phenyl, biphenyl, terphenyl, naphthyl, anthracenyl, or phenanthracenyl, a nitro-substituted aryl, or a bulky alkyl, such as a tert-butyl group. Such substituted pyrrole carboxaldehydes (II) are readily formed by formylation of an appropriately substituted pyrrole. This is conventionally accomplished by reacting the substituted pyrrole with an aldehyde source, such as formaldehyde (e.g., paraformaldehyde, 1,3,5-trioxane) in the presence of stannous chloride catalyst according to the procedures described by Casirighi et al in J. Chem. Soc. Perkins Trans. I, 1980, 1862–5, the teachings of which are incorporated herein by reference in its entirety.

As indicated above, $R^1$ may be selected from sterically bulky groups other than hydrocarbyl groups as, for example, siloxane groups. Such substitution can be readily accomplished by using a 5-hydroxy-2-carboxaldehyde pyrrole as the starting material II to form the Schiff base aldimine compound IV. The hydroxyl group can then be converted to a siloxy group by reaction with the appropriate aryl, alkyl or mixed substituted silyl halide as, for example triisopropyl silyl chloride, diphenyl-t-butyl silyl chloride, triphenyl silyl chloride and the like. Deprotonation and reaction with transition metal coordination compound of the type $R^5(L)_2$ MY provides the desired catalyst compound I in the manner described above.

As defined above, $R^1$ and $R^5$ may each independently be selected from a hydrocarbyl terminated oxyhydrocarbylene containing group. Such groups may be represented as —$(BO)_zR^7$ wherein each B is independently selected from a $C_1$–$C_4$ (preferably a $C_2$–$C_3$) alkylene group or an arylene group and $R^7$ represents a $C_1$–$C_{11}$ (preferably $C_1$–$C_3$) hydrocarbyl group such as alkyl, an aryl, an alkaryl, or an aralkyl group and z represents an integer of 1 to 4. Such oxyhydrocarbylene group may be made part of compound I by by mono-alkylation of 2-(2-hydroxyphenyl)-pyrrole or the N-protected 2-hydrophenylpyrrole with bromoethyl ether, followed by formayltion of the pyrrole ring adjacent to the nitrogen, followed by imine formation and finally metallation with $R^6(L)_2MY$ in the manner described previously.

It has been found that substituted pyrrolaldimine complexes (I) of late transition metals described above provide a catalytic composition having catalytic activity for olefin (e.g., ethylene) oligomerization or polymerization and provide substantially linear product having a low degree of branching. These complexes are neutral compounds and, as such do not require the presence of organo aluminum or hydrolyzed organo aluminum compounds or other reducing agent to cause activation of the complex towards olefin insertion reaction and polymerization. However, organo aluminum and hydrolyzed organo aluminum compounds, such as methyl alumoxane or trialkyl aluminum compounds and the like, may be present and are preferably present when $R^6$ is halogen. Compounds I are a new family of complexes of single-site catalysts.

The subject catalysts (I) may be used as the sole catalyst component of the catalyst composition (this is especially acceptable when the bulky group $R^1$ is large such as phenyl, biphenyl, terphenyl, anthracenyl, phenanthracenyl, nitro-substituted aryl or the like) or may be used in combination with an adjunct agent and/or a Lewis base. The adjunct agent comprises known phosphine sponge material capable of facilitating phosphine (ligand L) dissociation and trapping of free phosphine. Such catalyst composition adjunct agents are, for example, bis(cyclooctadiene)-nickel, tris (pentafluorophenyl) boron, 9-borabicyclo[3.3.1]nonane (9-BBN), methyl iodide and the like.

It has unexpectedly been found that the subject catalyst provides an enhanced catalyst composition when combined with a Lewis base as, for example ethers, esters, aldehydes, ketones, alcohols, amides, organo carbonates, organonitro compounds, or mixtures thereof and even water. It is commonly believed that organometallic catalysts should be combined with Lewis acid compounds to provide effective catalyst systems and that water acts as a poison to such catalysts. In contrast to the present unexpected finding, it has been previously deemed important to use conventional single site catalysts, such as metallocene catalysts, in the absence of moisture or other oxygenated compounds in order to provide an effective catalyst system.

The Lewis base additives found useful in forming a catalyst composition with the catalyst of compound I or V comprise ether compounds, such as dialkyl ethers where each alkyl group is independently selected from a $C_1$–$C_{18}$ alkyl, preferably a $C_1$–$C_5$ alkyl group as, for example, diethyl ether, methyl ethyl ether, diisopropyl ether, ethyl propyl ether, dibutyl ether and the like; vinyl ethers such as ethyl vinyl ether and the like; aryl ethers as, for example, dibenzyl ether, diphenyl ether, dinaphthyl ether and the like, mixed ethers as, for example, amyl phenyl ether, methyl benzohydryl ether, benzyl phenyl ether, anisole, phenetole and the like. The ether additive may also be selected from cyclic ethers as, for example, tetrahydrofuran, dioxane-1,4, dioxane-1,3, crown ethers such as 18-crown-6, 14-crown-5, 12-crown-4 and the like as well as polyethers such as dimethoxyethane, diglyme, triglyme, pentaglyme or polyoxyalkylenes as, for example, polyoxyethylene (preferably lower molecular weight polymers which are miscible in the polymerization solvent used).

The above ethers, especially the alkyl and/or aryl group containing ethers and cyclic ethers described above, and most preferably dialkyl ether (e.g., diethyl ether) and low molecular weight polyethers (e.g., dimethoxyethane) have been found to be effective solvents or co-solvents for use in the polymerization process when the subject catalyst of compound I or compound V is used, as described herein below.

The Lewis base may be selected from an organic ester represented by the formula

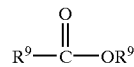

wherein each $R^9$ is independently selected from a $C_1$–$C_{11}$ alkyl group, preferably a $C_1$–$C_5$ alkyl group as, for example, ethyl acetate, propyl acetate, hexyl acetate, ethyl butyrate, propyl butyrate, ethyl caproate, ethyl caprylate, ethyl laurate and the like.

Further, aldehydes and ketones have been found useful as a Lewis base additive in forming the subject catalyst composition. They may be represented by the formula

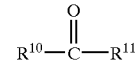

wherein $R^{10}$ represents a $C_1$–$C_{12}$ hydrocarbyl selected from unsubstituted or substituted (e.g., carbonyl) alkyl, aryl, alkaryl or aralkyl groups and $R^{11}$ represents a hydrogen atom or an $R^{10}$ group, which is independently selected. For example, the aldehyde or ketone may be selected from acetone, propanone, butyrone, 4-heptanone, 2,4-pentanedione and the like, as well as cyclic ketones such as cyclohexanone, 1,4-cyclohexanedione and the like, or an aldehyde such as acetaldehyde, capraldehyde, valeraldehyde and the like.

Still further, an alcohol can be used as the Lewis base additive in forming the subject catalyst composition. They may be selected from monohydric or polyhydric alcohols including, for example, alcohols having hydrocarbyl moiety composed of a $C_1$–$C_{12}$ (preferably $C_1$–$C_3$) alkyl, aryl (e.g., phenyl or benzyl), alkaryl and aralkyl groups. Examples of such alcohols include methanol, ethanol, propanol, isopropanol, butanol, t-butanol, 2-pentanol, 3-hexanol, glycol, 1,2,3-propanetriol, phenol, phenethyl alcohol, para-methyl phenol and the like.

Amides can be used as the Lewis base additive in forming the subject catalyst composition. The amides may be represented by the formula

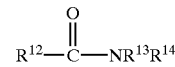

wherein $R^{12}$ and $R^{13}$ each independently represent a $C_1$–$C_{11}$ hydrocarbyl, $R^{14}$ represents hydrogen or a $C_1$–$C_{11}$ hydrocarbyl. $R^{13}$ and $R^{14}$ are, preferably, independently selected from a $C_1$–$C_3$ alkyl group.

Nitroalkanes and nitroaromatics have also been found to be useful as a Lewis base additive in forming the subject catalyst composition. The nitroalkanes may be a mono (preferred) or poly nitro compound formed with a $C_1$–$C_{11}$ (preferably a $C_1$–$C_3$) alkyl group. The aromatic nitro should be a mono nitro compound such as nitrobenzene and the like.

It has been unexpectedly found that the subject catalyst composition may contain small amounts of water and that the presence of water does not destroy the activity of the catalyst of the subject invention. Thus, unlike most organometallic catalysts useful in olefin polymerization, the presently described catalyst can be used in the presence of small amounts of moisture to provide a catalyst composition which can remain active in the polymerization or oligomerization of olefins or mixtures of olefins and a functional olefin monomer(s).

The amount of the Lewis base (except water) additive can be substantially any amount desired with from $10^0$ to $10^4$ times the amount of compound I or V on a molar base being preferred and, most preferred, from $10^1$ to $10^1$ times the molar amount of catalyst when ether is the Lewis base used and from $10^0$ to $10^2$ times the molar amount of catalyst with respect to other Lewis bases. In the case of water, the molar ratio of water to catalyst can range from 0 to about $10^2$, preferably, from 0 to $10^1$.

This invention concerns processes for making polymers, comprising, contacting the subject catalyst composition with one or more selected olefins or cycloolefins, alone or optionally with a functional α-olefin such as a carboxylic acid of the formula $CH_2=CH(CH_2)_mCOOH$, a carboxylic acid ester of the formula $CH_2=CH(CH_2)_mCO_2R^7$ or $CH_2=CHOCOR^7$, an alkyl vinyl ether of the formula $CH_2=CH(CH_2)_mOR^7$, vinyl ketones of the formula $CH_2=CH(CH_2)_mC(O)R^7$, a vinyl alcohol of the formula $CH_2=CH(CH_2)_mOH$, or a vinyl amine of the formula $CH_2=CH(CH_2)_mNR^8{}_2$, wherein m is an integer of 0 to 10 and $R^7$ is a $C_1$–$C_{10}$ hydrocarbyl group, aryl or substituted aryl group (preferably methyl) and $R^8$ is independently selected from hydrogen or an $R^7$ group; a functional cycloolefin, such as functionalized norbornene wherein the functional group is an ester, alcohol, carboxylic acid, halogen atom, primary, secondary or tertiary amine group or the like; or unsaturated dicarboxylic acid anhydride or carbon monoxide or the like and other selected monomers, such as vinyl halides. The subject catalyst composition is composed of the subject transition metal containing compound (I) described above or a combination of compound (V) and transition metal complex, as described herein below. The "polymerization process" described herein (and the polymers made therein) is defined as a process which produces a polymer or oligomer with a weight average molecular weight (Mw) of at least about 150, preferably at least about 1000.

The subject catalysts may generally be written as

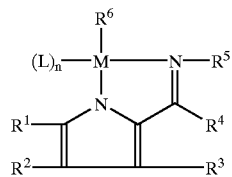

(I)

wherein each symbol $R^1$, $R^2$, $R^3$, $R^4$, $R^5$, $R^6$, L, and M are defined above. Preferably M is Ni(II) or Pd(II).

Alternately, the catalytic polymerization of the present invention can be carried by contacting one or more selected olefins or cycloolefins alone or optionally with a functional olefin monomer, as described above with a catalyst composition composed of one or more bidentate ligand (V) described above in combination with a transition metal (M) organic complex. The ligand (V) and complex should be used in about a 1:1 molar ratio. In a preferred embodiment of the present invention, the bidentate ligand V is combined with a transition metal organic complex of the formula $R^6(L)_2MY$ in about a 1:1 molar ratio in the presence of olefin and/or cycloolefin alone or optionally with a functional olefin monomer. The catalyst composition composed of ligand (V) and transition metal organic complex may further contain a phosphine sponge and/or Lewis base additive, such as those described above, or an organo aluminum or hydrolyzed organo aluminum compound or mixtures thereof as described above with respect to catalyst compositions composed of compound (I) which have a halogen as $R^6$.

In all catalysts and precursor bidentate ligands, described herein, it is preferred that $R^1$ and $R^5$ are each independently a sterically bulky hydrocarbyl. In one form it is especially preferred that $R^1$ and $R^5$ are each independently aryl or substituted aryl groups. In another form, it is preferred that $R^1$ and/or $R^5$ be independently selected from a hydrocarbyl terminated oxyhydrocarbylene containing group, as described above. It is preferred that when $R^5$ is a substituted aryl the 4 position of the aryl (with respect to the N-bond) be either hydrogen or nitro.

When using I or V as a catalyst, it is preferred that $R^2$, $R^3$ and $R^4$ are hydrogen or methyl, unless $R^2$ is, when taken together with $R^1$, a $C_4$–$C_{10}$ carbocyclic group which may or may not be aromatic. It is also preferred that either or both $R^1$ and $R^5$ are biphenyl, terphenyl, anthracenyl, phenanthracenyl, 2,6-diisopropylphenyl, 2,6-dimethylphenyl, 2,6-diethylphenyl, 4-methylphenyl, 2-isopropyl-6-methylphenyl, phenyl, 2,4,6-trimethylphenyl, 2-t-butylphenyl, 2-t-butyl-6-methylphenyl, 2,6-diisopropyl-4-nitrophenyl, and 10-nitroanthracenyl.

The structure of the ligand associated with compound I or compound V may influence the polymer microstructure and polymer molecular weight. For example, it is preferred that $R^1$ be a bulky aryl or substituted aryl group. Complexes with $R^1$ of this type generally produce higher molecular weight and more linear polymer product for any given set of conditions.

The catalyst or catalyst composition of I or V with the phosphine sponge adjunct or organo aluminum compound adjunct or with the Lewis base additive or mixtures of adjunct and Lewis base, when optionally used, are contacted, usually in a liquid phase, with ethylene or other alpha-olefin ($RCH=CH_2$), and/or 4-vinylcyclohexane, 4-vinylcyclohexene, cyclopentene, cyclobutene, substituted norbornene, or norbornene. The liquid phase may include a compound added just as a solvent and/or may include the monomer(s) itself and/or may comprise the Lewis base (especially an ether compound) in the liquid phase at reaction conditions. When an adjunct is used, the molar ratio of adjunct to compound I or V is from about 0.001:1 to 15:1, preferably about 0.01:1 to about 8:1 and most preferably from 0.1:1 to 3:1. The temperature at which the polymerization is carried out is from about −100° C. to about +200°C., preferably about −20°C. to about +100° C. and most preferably between about 0° C. and 90°C. All ranges of temperatures between −100 and +200°C. being covered by this teaching. The pressure at which the polymerization is carried out is not critical, atmospheric pressure to about 100 MPa, or more, being a suitable range. The pressure may affect the yield, molecular weight and linearity of the polyolefin produced, with increased pressure providing higher molecular weight, more linear oligomer or polymer product.

Preferred alpha-olefins and cyclic olefins in the polymerization are one or more of ethylene, propylene, 1-butene, 2-butene, 1-hexene, 1-octene, 1-pentene, 1-tetradecene, norbornene, and cyclopentene, with ethylene, propylene, cyclopentene and norbornene being more preferred. Ethylene (alone as a monomer) is especially preferred.

The polymerization may be run in the presence of various liquids. The solvent in which the polymerization may be conducted can be selected from (i) the monomer(s), per se or (ii) any organic compound which is liquid under the reaction conditions and is substantially inert to the reactants and product, or (iii) a Lewis base additive (except water which, when used, should be present in limited amounts) which is liquid under the reaction conditions, or mixtures thereof. Particularly preferred are aprotic organic liquids or organic ethers or mixtures thereof. The catalyst system, monomer(s), and polymer may be soluble or insoluble in these liquids, but obviously these liquids should not prevent the polymerization from occurring. Suitable liquids include alkanes, cycloalkanes, halogenated hydrocarbons, ethers, halogenated aromatic hydrocarbons and aromatic hydrocarbons. Specific useful solvents include hexane, heptane, toluene, xylenes, benzene, methylene chloride, ethyl ether, dimethoxyethane, tetrahydrofuran and crown ethers.

The catalyst compositions of the present invention cause polymerization of one or more alpha-olefin, with functional olefins such as those described herein above. When carbon monoxide is used as a comonomer, it forms alternating copolymers with the various alpha-olefins. The polymerization to form the alternating copolymers is carried out with both CO and the olefin simultaneously present in the process mixture, and in the presence of the present catalyst composition.

The catalyst of the present invention may also be supported on a solid material (as opposed to just being added as a suspended solid or in solution), for instance on silica gel, zeolites, crosslinked organic polymers, such as styrene-divinylbenzene copolymer and the likes thereof. By supported is meant that the catalyst may simply be carried physically on the surface of the solid support, may be adsorbed, or may be carried by the support by other means.

In many of the polymerizations, certain general trends may occur, although for all of these trends there are exceptions. Pressure of the monomers (especially gaseous monomers such as ethylene) has an effect on the polymerizations in many instances. Higher pressure often reduces branching and extends polymer chain length, especially in ethylene containing polymers. Temperature also affects these polymerizations. Higher temperature usually increases branching.

In general, the period of time during which the catalyst of compound I or the catalyst composition formed from compound V, remains active is influenced by the particular ligand structure, polymerization temperature, or type of Lewis base present. Catalyst lifetime is long when Lewis base such as ether is present, co-catalyst adjunct is absent, and $R^1$ is a bulky aryl or substituted aryl group.

When the polymer product of the present invention is a copolymer of functionalized group containing monomer, the functional group may be further used to cross-link the polymer. For example, when copolymers of an olefinic carboxylic acid or olefinic ester and an alpha-olefin are made, they may be crosslinked by various methods known in the art, depending on the specific monomers used to make the polymer. For instance, carboxyl or ester containing polymers may be crosslinked by reaction with diamines or with diisocyanates to form bisamides. The carboxyl groups may also be neutralized with a monovalent or divalent metal containing base (e.g., NaOH, CaO) to form ionomeric or pseudo-crosslinked polyolefin copolymer.

The resultant polymers formed according to the present invention, especially those of ethylene homo or copolymers may have varying degrees of branching in the polymer. Branching may be determined by NMR spectroscopy (see the Examples for details), and this analysis can determine the total number of branches, the branching distribution and to some extent the length of the branches. Herein the amount of branching is expressed as the number of branches per 1000 of the total methylene ($-CH_2-$) groups in the polymers, with one exception. Methylene groups that are in an ester grouping, i.e., $-CO_2R$; a ketone group, i.e., $-C(O)R$ are not counted as part of the 1000 methylenes. The polymers formed with the aid of the present catalyst have low branching of from about 10 to 150 branches per 1000, and normally from about 20 to 120 branches per 1000, for example, ethylene homopolymers have a branch content of about 0 to about 150 branches per 1000 methylene groups, preferably about 5 to about 100 and most preferably about 3 to about 70 branches per 1000 methylene groups. These branches do not include polymer end groups.

The polymers formed by the present invention may be mixed with various additives normally added to elastomers and thermoplastics [see EPSE (below), vol. 14, p. 327–410] which teaching is incorporated herein by reference. For instance reinforcing, non-reinforcing and conductive fillers, such as carbon black, glass fiber, minerals such as silica, clay, mica and talc, glass spheres, barium sulfate, zinc oxide, carbon fiber, and aramid fiber or fibrids, may be used. Antioxidants, antiozonants, pigments, dyes, slip agents, anti-fog agents, antiblock agents, delusterants, or compounds to promote crosslinking may be added. Plasticizers such as various hydrocarbon oils may also be used.

The polymers formed by the present invention may be used for one or more of the applications listed below. In some cases a reference is given which discusses such uses for polymers in general. All of these references are hereby included by reference. For the references, "U" refers to W. Gerhartz, et al., Ed., Ullmann's Encyclopedia of Industrial Chemistry, 5th Ed. VCH Verlagsgesellschaft mBH, Weinheim, for which the volume and page number are given, "ECT3" refers to the H. F. Mark, et al., Ed., Kirk-Othmer Encyclopedia of Chemical Technology, 4th Ed., John Wiley & Sons, New York, "ECT4" refers to the J. I. Kroschwitz, et al., Ed., Kirk-Othmer Encyclopedia of Chemical Technology, 4th Ed., John Wiley & Sons, New York, for which the volume and page number are given. "EPST" refers to H. F. Mark, et al., Ed., Encyclopedia of Polymer Science and Technology, 1st Ed., John Wiley & Sons, New York, for which the volume and page number are given, "EPSE" refers to H. F. Mark, et al., Ed., Encyclopedia of Polymer Science and Engineering, 2nd Ed., John Wiley & Sons, New York, for which volume and page numbers are given, and "PM" refers to J. A. Brydson, ed., Plastics Materials, 5th Ed., Butterworth-Heinemann, Oxford, UK, 1989, and the page is given. In these uses, a polyethylene, polypropylene and a copolymer of ethylene and propylene are preferred.

1. The polyolefins herein are especially useful in blown film applications because of their particular Theological properties (EPSE, vol. 7, p. 88–106). It is preferred that these polymers have some crystallinity.
2. The polymers are useful for blown or cast films or as sheet (see EPSE, vol. 7 p. 88–106; ECT4, vol. 11, p 843–856; PM, p. 252 and p. 432ff). The films may be single layer or multilayer, the multilayer films may include other polymers, adhesives, etc. For packaging the films may be stretch-wrap, shrink-wrap or cling wrap and may be heat sealable. The films are useful for many applications such as packaging foods or liquids, geomembranes and pond liners. It is preferred that these polymers have some crystallinity.
3. Extruded films or coextruded films may be formed from these polymers, and these films may be treated, for example by uniaxial or biaxial orientation after crosslinking by actinic radiation, especially electron beam irradiation. Such extruded films are useful for packaging of various sorts. The extruded films may also be laminated to other films using procedures known to those skilled in the art. The laminated films are also useful for packaging of various sorts.
4. The polymers, particularly the elastomers, may be used as tougheners for other polyolefins such as polypropylene and polyethylene.
5. Tackifiers for low strength adhesives (U, vol. Al, p 235–236) are a use for these polymers. Elastomers and/or relatively low molecular weight polymers are preferred.

6. An oil additive for smoke suppression in single-stroke gasoline engines is another use. Elastomeric polymers are preferred.
7. The polymers are useful as base resins for hot melt adhesives (U, vol. Al, p 233–234), pressure sensitive adhesives (U, vol. Al, p 235–236) or solvent applied adhesives. Thermoplastics are preferred for hot melt adhesives.
8. Base polymer for caulking of various kinds is another use. An elastomer is preferred. Lower molecular weight polymers are often used.
9. Wire insulation and jacketing may be made from any of the polyolefins (see EPSE, vol. 17, p. 828–842). In the case of elastomers it may be preferable to crosslink the polymer after the insulation or jacketing is formed, for example by free radicals.

The following examples are provided herein below for illustrative purposes only and are not meant to be a limitation on the scope of the invention. All parts and percentages are by weight unless otherwise indicated.

EXAMPLE I

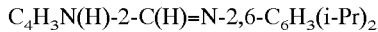

To a benzene (50 mL) solution of 2-pyrrolecarboxaldehyde (5.0 g, 54 mmol) was added 2,6-diisopropylaniline (12 g, 70 mmol) and p-toluenesulfonic acid (40 mg). The reaction was stirred under reflux for 24 hours. After this time, the solution was concentrated under vacuum to yield a red-brown oil. Methanol (30 mL) was added to the oil which resulted in precipitation of a white solid. The solid was isolated by filtration through a glass frit and washed with additional methanol to yield 6.8 g (50%) of a white solid. $^1$H NMR ($C_6D_6$): δ1.10 (d, 12H, $J_{HH}$=6.90 Hz), 3.06 (septet, 2H, $J_{HH}$=6.90 Hz), 6.17 (br s, 1H), 6.40 (t, 1H, $J_{HH}$=2.54 Hz), 6.61 (d, 1H, $J_{HH}$=2.54 Hz), 7.10–7.18 (m, 3H), 7.95 (s, 1H); $^{13}$C NMR ($C_6D_6$): δ23.6, 27.9, 109.8, 116.7, 123.2, 124.2, 124.5, 129.8, 139.0, 148.4, 152.7.

EXAMPLE II

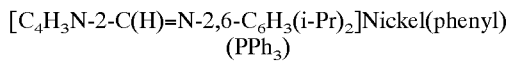

In a Schlenk flask was dissolved the Li salt of the product from Example I (0.24 g, 0.72 mmol) and bis(triphenylphosphine)nickel(phenyl)chloride (0.50 g, 0.73 mmol) in $Et_2O$ (20 mL). The reaction was stirred at room temperature for 1 hour. After this time, the reaction was filtered by cannula filtration, and the filtrate was concentrated in vacuo to ~5 mL. Pentane (30 mL) was added and the reaction was cooled to −78° C. A yellow-orange solid precipitated from solution, and was isolated by cannula filtration to yield 0.35 g (74.0%) of a yellow-orange solid. $^1$H NMR ($C_6D_6$): δ1.11 (d, 6H, $J_{HH}$=6.77 Hz), 1.30 (d, 6H, $J_{HH}$=6.77 Hz), 3.96 (septet, 2H, $J_{HH}$=6.77 Hz), 6.17 (br s, 1H), 6.40 (t, 1H, $J_{HH}$=2.54 Hz), 6.61 (d, 1H, $J_{HH}$=2.54 Hz), 5.96–7.65 (m, 26H); $^{13}$C NMR ($C_6D_6$): δ22.6, 26.1, 28.9, 113.3, 117.9, 121.6, 122.6, 125.8, 125.9, 130.0, 130.1, 132.1, 132.7, 134.8 (d, $J_{CP}$=10.8 Hz), 136.8, 140.3, 141.3, 142.4, 146.5, 162.3; $^{31}$P NMR ($C_6D_6$): δ33.10. Anal. Calcd for $C_{41}H_{41}N_2NiP$: C, 75.59; H, 6.34; N, 4.30. Found: C, 75.74; H, 6.41; N, 4.15.

EXAMPLE III 1.8 mM of the catalyst product formed in Example II above was weighed out and introduced into a pressure container under an atmosphere of nitrogen. The container was evacuated and backfilled with ethylene. 80 mL of dry toluene was then cannula transferred into the pressure container. 5 mL of toluene solution containing 2 meq. of a phosphine sponge adjunct, bis(cyclooctadiene)-nickel was syringed into the container. Additional ethylene was introduced to raise the pressure to 80 psi at 25° C. The reaction was allowed to proceed with stirring for 40 minutes. After completion of the polymerization, methanol (500 mL) was introduced to terminate the reaction. No precipitate was recovered. The reaction solution was analyzed by gas chromatography using standard analytical techniques. The reaction mixture was found to contain a mixture of $C_{12}$–$C_{120}$ hydrocarbons.

What is claimed is:
1. A process for forming a polyolefin comprising contacting at least one olefinic compound with a catalyst composition comprising a compound represented by the general formula:

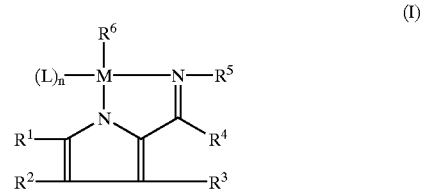

wherein
$R^1$ represents a $C_1$–$C_{11}$ alkyl; aryl; substituted aryl wherein the substitution group is selected from $C_1$–$C_4$ alkyl, perfluoroalkyl, nitro, sulfonate or halo group; arylalkyl; siloxyl (—$OSiA_3$ where A is selected from phenyl or $C_1$–$C_4$ alkyl); nitro group; sulfonate group; or halo atom;

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom, a $C_1$–$C_{11}$ alkyl; an aryl; substituted aryl group; or $R^3$ or $R^{4,}$ together, provide a hydrocarbylene or substituted hydrocarbylene forming a non-aromatic carbocyclic ring;

$R^5$ represents a $C_1$–$C_{11}$ alkyl; $C_5$–$C_8$ cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy or $C_1$–$C_4$ alkyl or fused or unfused aryl;

n represents an integer of 0 or 1;

$R^6$ represents, when n is 1, an unsubstituted or substituted aromatic group; a $C_1$–$C_{11}$ alkyl; a hydrogen atom or halogen atom or, when n is 0, $R^6$ represents an allyl group or substituted allyl group;

L represents a coordination ligand selected from triphenylphosphine, tri($C_1$–$C_6$ alkyl) phosphine tricycloalkyl phosphine, diphenyl alkyl phosphine, dialkyl phenylphosphine, triphenoxyphosphine, trialkylamine, $C_2$–$C_{20}$ alkene, substituted $C_2$–$C_5$ alkene, diethyl ether, ethyl propyl ether, tetrahydrofuran, or a nitrile; and M represents a Group IV or VIII transition metal selected from Fe, Co, Ni, Ru, Rh, Pd, Os, Ir, Pt in the +2 oxidation state.

2. The process of claim 1 wherein the catalyst composition further comprises a phosphine sponge.

3. The process of claim 1 wherein $R^6$ represents halogen atom and the composition further comprises a catalyst adjunct selected from a partially hydrolyzed aluminum alkyl compound or an aluminum alkyl or mixture thereof.

4. The process of claim 3 wherein the catalyst adjunct is selected from methyl alumoxane or trialkyl-aluminum or mixture thereof.

5. The process of claim 1 wherein $R^1$ is selected from aryl group, substituted aryl group or $C_3$–$C_6$ alkyl group.

6. The process of claim 2 or 3 wherein $R^1$ is selected from aryl group, substituted aryl group or $C_3$–$C_6$ alkyl group.

7. The process of claim 5 wherein $R^5$ is selected from an aryl group having one or both ortho positions substituted with a $C_1$–$C_4$ alkyl group.

8. The process of claim 6 wherein $R^5$ is selected from an aryl group having one or both ortho positions substituted with a $C_1$–$C_4$ alkyl group.

9. The process of claim 5 wherein $R^5$ is selected from alkyl or cycloalkyl.

10. The process of claim 5 wherein $R^5$ is selected from alkyl or cycloalkyl.

11. The process of claim 1, 2, 3, 4, or 5 wherein M is nickel or palladium atom.

12. The process of claim 11 wherein the olefinic compound is selected from a $C_2$–$C_3$ olefinic compound.

13. The process of claim 12 wherein the olefinic compound is ethylene.

14. The process of claim 12 wherein the olefinic compound further comprises at least one functionalized alpha-olefin selected from a carboxylic acid of the formula $CH_2$=$CH(CH_2)_m COOH$, an alkyl vinyl ether of the formula $CH_2$=$CH(CH_2)_m OR^7$, vinyl ketones of the formula $CH_2$=$CH(CH_2)_m C(O)R^7$, vinyl alcohol of the formula $CH_2$=$CH(CH_2)_m OH$, vinyl amine of the formula $CH_2$=$CH(CH_2)_m NR^8_2$, wherein m is an integer of 0 to 10 and $R^7$ is a $C_1$–$C_{10}$ hydrocarbyl, aryl or substituted aryl group and each $R^8$ is independently selected from hydrogen atom or a $R^7$ group; a cycloolefin having a functional group selected from an ester, carboxylic acid, halogen atom, or amine group; unsaturated dicarboxylic acid anhydride; carbon monoxide; vinyl halide; or mixtures thereof.

15. A process for forming a polyolefin comprising contacting at least one olefinic compound with a catalyst composition comprising a compound represented by the general formula:

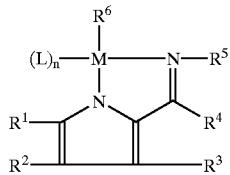

(I)

wherein $R^1$ represents a $C_1$–$C_{11}$ alkyl; aryl; substituted aryl wherein the substitution group is selected from $C_1$–$C_4$ alkyl, perfluoroalkyl, nitro, sulfonate or halo group; arylalkyl; siloxyl (—$OSiA_3$ where A is selected from phenyl or $C_1$–$C_4$ alkyl); nitro group; sulfonate group; halo atom; or a hydrocarbyl terminated oxyhydrocarbylene group (—$(BO)_z R^7$) wherein each B independently is selected from a $C_1$–$C_4$ alkylene or an arylene group, O represents oxygen, $R^7$ represents a $C_1$–$C_{11}$ hydrocarbyl group and z is an integer of 1 to 4;

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom; a $C_1$–$C_{11}$ alkyl; an aryl; substituted aryl group; or $R^3$ or $R^4$, together, provide a hydrocarbylene or substituted hydrocarbylene forming a non-aromatic carbocyclic ring;

$R^5$ represents a $C_1$–$C_{11}$ alkyl; $C_5$–$C_8$ cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy or $C_1$–$C_4$ alkyl, sulfonate or fused or unfused aryl group, or a hydrocarbyl terminated oxyhydrocarbylene group (—$BO$—)$_z R^7$ with B, O, $R^7$ and z, as defined above with respect to $R^1$; or $R^1$ and $R^5$ together form an oxyhydrocarbylene chain (—$(BO)_m B$—) wherein each B is independently selected from a $C_1$–$C_4$ alkylene or an arylene group and m is an integer of 1–4;

n represents an integer of 0 or 1;

$R^6$ represents, when n is 1, an unsubstituted or substituted aromatic group; a $C_1$–$C_{11}$ alkyl; a hydrogen atom or halogen atom or, when n is 0, $R^6$ represents an allyl group or substituted allyl group;

L represents a coordination ligand selected from triphenylphosphine, tri($C_1$–$C_6$ alkyl) phosphine, tricycloalkyl phosphine, diphenyl alkyl phosphine, dialkyl phenylphosphine, triphenoxyphosphine, trialkylamine, pyridine, $C_2$–$C_{20}$ alkene, substituted $C_2$–$C_5$ alkene, $C_1$–$C_{11}$ alkoxy, di($C_1$–$C_3$ alkyl) ether, tetrahydrofuran, or a nitrile; and M represents a Group IV or VIII transition metal selected from Fe, Co, Ni, Ru, Rh, Pd, Os, Ir, Pt in the +2 oxidation state.

16. The process of claim 15 wherein the catalyst composition further comprises a phosphine sponge.

17. The process of claim 15 wherein $R^6$ represents halogen atom and the composition further comprises a catalyst adjunct selected from a partially hydrolyzed aluminum alkyl compound or an aluminum alkyl or mixture thereof.

18. The process of claim 17 wherein the catalyst adjunct is selected from methyl alumoxane or trialkyl-aluminum or mixture thereof.

19. The process of claim 15 wherein $R^1$ is selected from aryl group, substituted aryl group or $C_1$–$C_6$ alkyl group.

20. The process of claim 16 or 17 wherein $R^1$ is selected from aryl group, substituted aryl group or $C_3$–$C_6$ alkyl group.

21. The process of claim 19 wherein $R^5$ is selected from an aryl group having one or both ortho positions substituted with a $C_1$–$C_4$ alkyl group.

22. The process of claim 20 wherein $R^5$ is selected from an aryl group having one or both ortho positions substituted with a $C_1$–$C_4$ alkyl group.

23. The process of claim 19 wherein $R^5$ is selected from alkyl or cycloalkyl.

24. The process of claim 20 wherein $R^5$ is selected from alkyl or cycloalkyl.

25. The process of claim 15, 16, 17, 18, or 19 wherein M is nickel or palladium atom.

26. The process of claim 25 wherein the olefinic compound is selected from a $C_2$–$C_3$ olefinic compound.

27. The process of claim 26 wherein the olefinic compound is ethylene.

28. The process of claim 26 wherein the olefinic compound further comprises at least one functionalized alpha-olefin selected from a carboxylic acid of the formula $CH_2=CH(CH_2)_mCOOH$, an alkyl vinyl ether of the formula $CH_2=CH(CH_2)_mOR^7$, vinyl ketones of the formula $CH_2=CH(CH_2)_mC(O)R^7$, vinyl alcohol of the formula $CH_2=CH(CH_2)_mOH$, vinyl amine of the formula $CH_2=CH(CH_2)_mNR^8{}_2$, wherein m is an integer of 0 to 10 and $R^7$ is a $C_1$–$C_{10}$ hydrocarbyl, aryl or substituted aryl group and each $R^8$ is independently selected from hydrogen atom or a $R^7$ group; a cycloolefin having a functional group selected from an ester, carboxylic acid, halogen atom, or amine group; unsaturated dicarboxylic acid anhydride; carbon monoxide; vinyl halide; or mixtures thereof.

29. The process of claim 15 wherein the catalyst composition further comprises a phosphine sponge or a Lewis base or mixtures thereof.

30. The process of claim 15 wherein the catalyst composition further comprises a Lewis base selected from ethers, esters, aldehydes, ketones, alcohols, amides, organocarbonates and organonitro compounds and mixtures thereof.

31. The process of claim 29 wherein the Lewis base comprises water, said water present in a molar ratio of water to catalyst of from 0 to $10^2$.

32. The process of claim 30 wherein the Lewis base is an ether selected from a di($C_1$–$C_{18}$ alkyl) ether, aryl ethers, aryl alkyl ethers, cyclic ethers, polyethers, or mixtures thereof.

33. The process of claim 32 wherein the polymerization is carried out in solution and the polymerization solvent comprises an ether or polyether.

34. The process of claim 30 wherein the Lewis base is an organic ester represented by the formula:

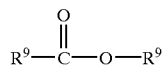

wherein each $R^9$ independently represents a $C_1$–$C_{11}$ alkyl group.

35. The process of claim 30 wherein the Lewis base is an aldehyde or ketone represented by the formula:

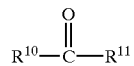

wherein $R^{10}$ represents an unsubstituted or substituted $C_1$–$C_{12}$ hydrocarbyl group and $R^{11}$ represents a hydrogen atom or an $R^{10}$ group.

36. The process of claim 30 wherein the Lewis base is a monohydric or polyhydric alcohol, said alcohol having hydrocarbyl group composed of a $C_1$–$C_{12}$ alkyl, aryl, alkaryl or aralkyl group.

37. The process of claim 30 wherein the Lewis base is an amide represented by the formula:

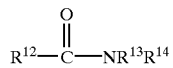

wherein $R^{12}$ and $R^{13}$ each independently represents a $C_1$–$C_{11}$ hydrocarbyl and $R^{14}$ represents hydrogen or a $C_1$–$C_{11}$ hydrocarbyl group.

38. The process of claim 30 wherein the Lewis base is an organonitro compound selected from $C_1$–$C_{11}$ nitroalkanes, $C_1$–$C_{11}$ polynitro alkanes, or mono-nitroaromatics.

39. The process of claim 30, 32, 34, 35, 36, 37 or 38 wherein the Lewis base is present in a molar ratio of Lewis base to catalyst compound I of from about $10^0$ to about $10^4$.

40. The process of claim 15 wherein $R^1$ is selected from a hydrocarbyl terminated oxyhydrocarbylene group represented by the formula —$(BO)_zR^7$ wherein each B is independently selected from a $C_1$–$C_4$ alkylene or an arylene group, O is oxygen, $R^7$ is a $C_1$–$C_{11}$ hydrocarbyl and z is 1–4.

41. The process of claim 15 wherein $R^5$ is selected from an aryl group substituted with a hydrocarbyl terminated oxyalkylene group represented by the formula —$(BO)_zR^7$ wherein B is a $C_1$–$C_4$ alkylene, O is oxygen, $R^7$ is a $C_1$–$C_{11}$ hydrocarbyl and z is 1–4.

42. The process of claim 15 wherein $R^5$ is selected from a 2,6-di($C_1$–$C_4$ alkyl) phenyl and $R^1$ is anthracenyl.

43. The process of claim 15 wherein $R^5$ is selected from a 2,6-di($C_1$–$C_4$ alkyl) phenyl and $R^1$ is phenanthracenyl.

44. The process of claim 15 wherein $R^5$ is selected from a 2,6-di($C_1$–$C_4$ alkyl) phenyl and $R^1$ is phenyl.

45. The process of claim 15 wherein $R^1$ and $R^5$ together represent a polyoxyhydrocarbylene group.

46. The process of claim 16, 17, 18, 19, 21, or 23 wherein the catalyst composition further comprises a Lewis base selected from ethers, esters, aldehydes, ketones, alcohols, amides, organocarbonates, organonitro compounds or mixtures thereof.

47. The process of claim 20 wherein the catalyst composition further comprises a Lewis base selected from ethers, esters, aldehydes, ketones, alcohols, amides, organocarbonates, organonitro compounds and mixtures thereof.

48. The process of claim 25 wherein the catalyst composition further comprises a Lewis base selected from ethers, esters, aldehydes, ketones, alcohols, amides, organocarbonates, organonitro compounds or mixtures thereof.

49. A process for forming a polyolefin comprising contacting at least one olefinic compound with a catalyst composition comprising:

(A) a compound represented by the formula:

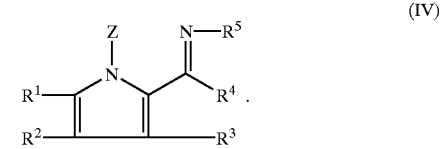

(IV)

wherein $R^1$ represents a $C_1$–$C_{11}$ alkyl; aryl; substituted aryl wherein the substitution group is selected from $C_1$–$C_4$ alkyl, perfluoroalkyl, nitro, sulfonate or halo group; arylalkyl; or siloxyl (—$OSiA_3$ where A is selected from phenyl or $C_1$–$C_4$ alkyl); nitro group; sulfonate group; or halo atom;

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom, a $C_1$–$C_{11}$ alkyl; an aryl; substituted aryl group; or $R^3$ and $R^4$, together, provide a hydrocarbylene or substituted hydrocarbylene forming non-aromatic carbocyclic ring;

$R^5$ represents a $C_1$–$C_{11}$ alkyl; cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy or $C_1$–$C_4$ alkyl or fused or unfused aryl; and Z represents hydrogen or an alkali metal; and (B) a transition metal organic complex, wherein said transition metal has a valence state of +2 or +4 and is selected from Group IV or VIII transition metal of Ti, Zr, Hf, Co, Ni, Ru, Rh, Pd, Os, Ir or Pt.

50. The process of claim 49 wherein the transition metal organic complex is a complex of a $C_5$–$C_{10}$ cycloalkyldiene, or a trihydrocarbyl phosphine wherein each hydrocarbyl group is independently selected from $C_1$–$C_{10}$ alkyl, cycloalkyl or phenyl group.

51. The process of claim 50 wherein the catalyst composition further comprises a phosphine sponge.

52. The process of claim 50 wherein the composition further comprises a catalyst adjunct selected from a partially hydrolyzed aluminum alkyl compound or an aluminum alkyl or mixture thereof.

53. The process of claim 52 wherein the catalyst composition further comprises an adjunct selected from methyl alumoxane or trialkyl-aluminum or mixture thereof.

54. The process of claim 50 wherein $R^1$ is selected from aryl group, substituted aryl group or $C_3$–$C_6$ alkyl group.

55. The process of claim 51 or 53 wherein $R^1$ is selected from aryl group, substituted aryl group or $C_3$–$C_6$ alkyl group.

56. The process of claim 54 wherein $R^5$ is selected from an aryl group having one or both ortho positions substituted with a $C_1$–$C_4$ alkyl group.

57. The process of claim 55 wherein $R^5$ is selected from an aryl group having one or both ortho positions substituted with a $C_1$–$C_4$ alkyl group.

58. The process of claim 54 wherein $R^5$ is selected from alkyl or cycloalkyl.

59. The process of claim 55 wherein $R^5$ is selected from alkyl or cycloalkyl.

60. The process of claim 49, 50, 51, 52 or 53 wherein the transition metal of said complex is selected from nickel or palladium atom.

61. The process of claim 60 wherein the olefinic compound is a $C_2$–$C_3$ olefinic compound.

62. The process of claim 61 wherein the olefinic compound is ethylene.

63. The process of claim 61 wherein the olefinic compound further comprises at least one functionalized alpha-olefin selected from a carboxylic acid of the formula $CH_2=CH(CH_2)_mCOOH$, an alkyl vinyl ether of the formula $CH_2=CH(CH_2)_mOR^7$, vinyl ketones of the formula $CH_2=CH(CH_2)_mC(O)R^7$, vinyl alcohol of the formula $CH_2=CH(CH_2)_mOH$, vinyl amine of the formula $CH_2=CH(CH_2)_mNR^8{}_2$, wherein m is an integer of 0 to 10 and $R^7$ is a $C_1$–$C_{10}$ hydrocarbyl, aryl or substituted aryl group and each $R^8$ is independently selected from hydrogen atom or a $R^7$ group; a cycloolefin having a functional group selected from an ester, carboxylic acid, halogen atom, or amine group; unsaturated dicarboxylic acid anhydride; carbon monoxide; vinyl halide; or mixtures thereof.

64. A process for forming a polyolefin comprising contacting at least one olefinic compound with a catalyst composition comprising:

(A) a compound represented by the formula:

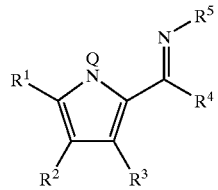

(V)

wherein $R^1$ represents a $C_1$–$C_{11}$ alkyl; aryl; substituted aryl wherein the substitution group is selected from $C_1$–$C_4$ alkyl, perfluoroalkyl, nitro, sulfonate or halo group; arylalkyl; or siloxyl (—$OSiA_3$ where A is selected from phenyl or $C_1$–$C_4$ alkyl); nitro group; sulfonate group; halo atom; or or a hydrocarbyl terminated oxyhydrocarbylene group (—$(BO)_zR^7$), wherein each B independently is selected from a $C_1$–$C_4$ alkylene or an arylene group, O represents oxygen, $R^7$ represents a $C_1$–$C_{11}$ hydrocarbyl group and z is an integer of 1 to 4;

$R^2$ represents hydrogen atom, aryl, substituted aryl, $C_1$–$C_{11}$ alkyl, halogen atom or $R^1$ and $R^2$, together, provide a hydrocarbylene or substituted hydrocarbylene which forms an aromatic or non-aromatic carbocyclic ring;

$R^3$ represents hydrogen;

$R^4$ represents hydrogen atom, a $C_1$–$C_{11}$ alkyl; an aryl; substituted aryl group; or $R^3$ or $R^4$, together, provide a hydrocarbylene or substituted hydrocarbylene forming a non-aromatic carbocyclic ring;

$R^5$ represents a $C_1$–$C_{11}$ alkyl; cycloalkyl; aryl group; a substituted aryl having one or both ortho positions of the aromatic group substituted with a $C_1$–$C_4$ alkyl, the para position (with respect to the N—$R^5$ bond) substituted with a hydrogen, nitro, trifluoromethyl, halogen, methoxy or $C_1$–$C_4$ alkyl or fused or unfused aryl; or a hydrocarbyl terminated oxyhydrocarbylene group (—BO—)$_zR^7$ with B, O, $R^7$ and z, as defined above with respect to $R^1$; or $R^1$ and $R^5$ together form an oxyhydrocarbylene chain (—$(BO)_mB$—) wherein each B is independently selected from a $C_1$–$C_4$ alkylene or an arylene group and m is an integer of 1–4); and Q is an alkali metal cation; and (B) a transition metal organic complex, wherein said transition metal has a valence state of +2 or +4 and is selected from a Group IV or VIII transition metal of Ti, Zr, Hf, Co, Ni, Ru, Rh, Pd, Os, Ir or Pt.

65. The process of claim 64 wherein the transition metal organic complex is a complex represented by a formula $R^6(L)_2MY$ wherein $R^6$ represents an unsubstituted or substituted aromatic group; a $C_1$–$C_{11}$ alkyl; an allyl or substituted allyl group;

L represents a coordination ligand selected from triphenylphosphine, tri ($C_1$–$C_6$ alkyl) phosphine, tricycloalkyl phosphine, diphenyl alkyl phosphine, dialkyl phenylphosphine, triphenoxyphosphine, trialkylamine, pyridine, $C_2$–$C_{20}$ alkene, substituted $C_2$–$C_4$ alkene, $C_1$–$C_4$ alkoxy, di-($C_1$–$C_3$ alkyl) ether, tetrahydrofuran, or a nitrile;

Y represents a halogen atom selected from chloro, bromo or fluoro; and

M represents a transition metal selected from a Group IV or Group VIII metal of Ti, Zr, Hf, Co, Ni, Ru, Rh, Pd, Os, Ir or Pt.

66. The process of claim 64 or 65 wherein the catalyst composition further comprises a phosphine sponge.

67. The process of claim 65 wherein the complex is bis-triphenylphosphine nickel (pheryl) chloride.

68. The process of claim 65 wherein the composition further comprises a catalyst adjunct selected from a partially hydrolyzed aluminum alkyl compound or an aluminum alkyl or mixture thereof.

69. The process of claim 68 wherein the catalyst composition further comprises an adjunct selected from methyl alumoxane or trialkylaluminum or mixture thereof.

70. The process of claim 64 wherein $R^1$ is selected from aryl group, substituted aryl group or $C_3$–$C_6$ alkyl group.

71. The process of claim 65 or 69 wherein $R^1$ is selected from aryl group, substituted aryl group or $C_3$–$C_6$ alkyl group.

72. The process of claim 70 wherein $R^5$ is selected from an aryl group having one or both ortho positions substituted with a $C_1$–$C_4$ alkyl group.

73. The process of claim 71 wherein $R^5$ is selected from an aryl group having one or both ortho positions substituted with a $C_1$–$C_4$ alkyl group.

74. The process of claim 70 wherein $R^5$ is selected from alkyl or cycloalkyl.

75. The process of claim 71 wherein $R^5$ is selected from alkyl or cycloalkyl.

76. The process of claim 64, 65, 67, 68 or 69 wherein the transition metal of said complex is selected from nickel or palladium atom.

77. The process of claim 76 wherein the olefinic compound is a $C_2$–$C_3$ olefinic compound.

78. The process of claim 77 wherein the olefinic compound is ethylene.

79. The process of claim 77 wherein the olefinic compound further comprises at least one funtionalized alpha-olefin selected from a carboxylic acid of the formula $CH_2=CH(CH_2)_m COOH$, an alkyl vinyl ether of the formula $CH_2=CH(CH_2)_m OR^7$, vinyl ketones of the formula $CH_2=CH(CH_2)_m C(O)R^7$, vinyl alcohol of the formula $CH_2=CH(CH_2)_m OH$, vinyl amine of the formula $CH_2=CH(CH_2)_m NR^8{}_2$, wherein m is an integer of 0 to 10 and $R^7$ is a $C_1$–$C_{10}$ hydrocarbyl, aryl or substituted aryl group and each $R^8$ is independently selected from hydrogen atom or a $R^7$ group; a cycloolefin having a functional group selected from an ester, carboxylic acid, halogen atom, or amine group; unsaturated dicarboxylic acid anhydride; carbon monoxide; vinyl halide; or mixtures thereof.

80. The process of claim 79 wherein the functionalized olefin is a hydroxyl substituted or ester substituted norbornene.

81. The process of claim 69 wherein the catalyst composition further comprises a phosphine sponge or a Lewis base or mixtures thereof.

82. The process of claim 69 wherein the catalyst composition further comprises a Lewis base selected from ethers, esters, aldehydes, ketones, alcohols, amides, organocarbonates and organonitro compounds and mixtures thereof.

83. The process of claim 81 wherein the Lewis base comprises water, said water present in a molar ratio of water to catalyst of from 0 to $10^2$.

84. The process of claim 82 wherein the Lewis base is an ether selected from di($C_1$–$C_{18}$ alkyl) ethers, aryl ethers, aryl alkyl ethers, cyclic ethers, polyethers, or mixtures thereof.

85. The process of claim 84 wherein the polymerization is carried out in solution and the polymerization solvent comprises an ether or polyether.

86. The process of claim 82 wherein the Lewis base is an organic ester represented by the formula:

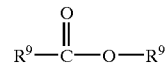

wherein each $R^9$ independently represents a $C_1$–$C_{11}$ alkyl group.

87. The process of claim 82 wherein the Lewis base is an aldehyde or ketone represented by the formula:

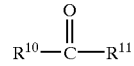

wherein $R^{10}$ represents an unsubstituted or substituted $C_1$–$C_{12}$ hydrocarbyl group and $R^{11}$ represents a hydrogen atom or an $R^{10}$ group.

88. The process of claim 82 wherein the Lewis base is a monohydric or polyhydric alcohol, said alcohol having a hydrocarbyl group composed of a $C_1$–$C_{12}$ alkyl, aryl, alkaryl or aralkyl group.

89. The process of claim 82 wherein the Lewis base is an amide represented by the formula:

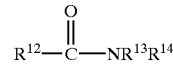

wherein $R^{12}$ and $R^{13}$ each independently represents a $C_1$–$C_{11}$ hydrocarbyl and $R^{14}$ represents hydrogen or a $C_1$–$C_{11}$ hydrocarbyl group.

90. The process of claim 82 wherein the Lewis base is an organonitro compound selected from $C_1$–$C_{11}$ nitroalkanes, $C_1$–$C_{11}$ polynitro alkanes, or mono-nitroaromatics.

91. The process of claim 82, 84, 86, 87, 88, 89 or 90 wherein the Lewis base is present in a molar ratio of Lewis base to compound V from about $10^o$ to about $10^4$.

92. The process of claim 64 wherein $R^1$ is selected from a hydrocarbyl terminated oxyhydrocarbylene group represented by the formula —$(BO)_z R^7$ wherein each B is independently selected from a $C_1$–$C_4$ alkylene or an arylene, O is oxygen, $R^7$ is a $C_1$–$C_{11}$ hydrocarbyl and z is 1–4.

93. The process of claim 69 wherein $R^5$ is selected from an aryl group substituted with a hydrocarbyl terminated oxyalkylene group represented by the formula —$(BO)_z R^7$ wherein B is a $C_1$–$C_4$ alkylene, O is oxygen, $R^7$ is a $C_1$–$C_{11}$ hydrocarbyl and z is 1–4.

94. The process of claim 64 wherein $R^5$ is selected from a 2,6-di($C_1$–$C_4$ alkyl) phenyl and $R^1$ is anthracenyl.

95. The process of claim 64 wherein $R^5$ is selected from a 2,6-di($C_1$–$C_4$ alkyl) phenyl and $R^1$ is phenanthracenyl.

96. The process of claim 64 wherein $R^5$ is selected from a 2,6-di($C_1$–$C_4$ alkyl) phenyl and $R^1$ is phenyl.

97. The process of claim 64 herein $R^1$ and $R^5$ together, represent a polyoxyhydrocarbylene group.

98. The process of claim 65, 67, 68, 69, 70, 72, 74, 76 or 77 wherein the catalyst composition further comprises a Lewis base selected from ethers, esters, aldehydes, ketones, alcohols, amides, organocarbonates, organonitro compounds or mixtures thereof.

99. The process of claim 66 wherein the catalyst composition further comprises a Lewis base selected from ethers, esters, aldehydes, ketones, alcohols, amides, organocarbonates, organonitro compounds or mixtures thereof.

100. The process of claim 71 wherein the catalyst composition further comprises a Lewis base selected from ethers, esters, aldehydes, ketones, alcohols, amides, organocarbonates, organonitro compounds or mixtures thereof.

101. The process of claim 73 wherein the catalyst composition further comprises a Lewis base selected from ethers, esters, aldehydes, ketones, alcohols, amides, organocarbonates, organonitro compounds or mixtures thereof.

102. The process of claim 75 wherein the catalyst composition further comprises a Lewis base selected from ethers, esters, aldehydes, ketones, alcohols, amides, organocarbonates, organonitro compounds or mixtures thereof.

103. The process of claim 15, 16, 17, 18, 19, 20, 21, 22, 23, 24, 29, 30, 31 32, 33, 34, 34, 36, 37, 38, 40, 41, 42, 43, 44, 45 or 47 wherein said compound is supported on a porous solid material.

104. The process of claim 25 wherein said compound is supported on a porous solid material.

105. The process of claim 26 wherein said compound is supported on a porous solid material.

106. The process of claim 27 wherein said compound is supported on a porous solid material.

107. The process of claim 28 wherein said compound is supported on a porous solid material.

108. The process of claim 39 wherein said compound is supported on a porous solid material.

109. The process of claim 46 wherein said compound is supported on a porous solid material.

110. The process of claim 48 wherein said compound is supported on a porous solid material.

111. The process of claim 64 wherein said catalyst composition further comprises a porous solid catalyst support material.

112. The process of claim 68 wherein said catalyst composition further comprises a porous solid catalyst support material.

113. The process of claim 69 wherein said catalyst composition further comprises a porous solid catalyst support material.

114. The process of claim 81 wherein said catalyst composition further comprises a porous solid catalyst support material.

115. The process of claim 82 wherein said catalyst composition further comprises a porous solid catalyst support material.

116. The process of claim 24 wherein the catalyst composition further comprises a Lewis base selected from ethers, esters, aldehydes, ketones alcohols, amides, organocarbonates, organonitro compounds or mixtures thereof.

117. The process of claim 26 wherein the catalyst composition further comprises a Lewis base selected from ethers, esters, aldehydes, ketones alcohols, amides, organocarbonates, organonitro compounds or mixtures thereof.

118. The process of claim 77 wherein the catalyst composition further comprises a Lewis base selected from ethers, esters, aldehydes, ketones alcohols, amides, organocarbonates, organonitro compounds or mixtures thereof.

119. The process of claim 20 wherein said compound is supported on a porous solid material.

120. The process of claim 22 wherein said compound is supported on a porous solid material.

121. The process of claim 24 wherein said compound is supported on a porous solid material.

122. The process of claim 47 wherein said compound is supported on a porous solid material.

123. The process of claim 76 wherein the catalyst composition further comprises a Lewis base selected from ethers, esters, aldehydes, ketones, alcohols, amides, organocarbonates, organonitro compounds and mixtures thereof.

124. The process of claim 77 wherein the catalyst composition further comprises a Lewis base selected from ethers, esters, aldehydes, ketones, alcohols, amides, organocarbonates, organonitro compounds and mixtures thereof.

125. The process of claim 1 or 15 wherein n is 1.

\* \* \* \* \*